United States Patent [19]

Oguchi et al.

[11] Patent Number: 4,738,843
[45] Date of Patent: Apr. 19, 1988

[54] ANTI-TUMOR SUBSTANCE OF IMMUNOGLOBULIN AND MELPHALAN AND PROCESS FOR PRODUCING THE SAME

[75] Inventors: Yoshiharu Oguchi, Tokyo; Koichi Niimura, Sayama; Takayoshi Fujii, Tokyo; Masahiko Fujii, Komae; Kenichi Matsunaga, Tokyo; Chikao Yoshikumi, Kunitachi, all of Japan

[73] Assignee: Kureha Kagaku Kogyo Kabushiki Kaisha, Tokyo, Japan

[21] Appl. No.: 5,302

[22] Filed: Jan. 20, 1987

Related U.S. Application Data

[63] Continuation of Ser. No. 595,037, Mar. 29, 1984, abandoned.

[30] Foreign Application Priority Data

Apr. 8, 1983 [JP] Japan ................................ 58-61923

[51] Int. Cl.$^4$ ............................................. A61K 39/44
[52] U.S. Cl. ........................................ 424/85; 424/88; 514/8; 530/388; 530/389; 530/390; 530/391
[58] Field of Search .............. 530/388, 390, 391, 389; 424/85, 88; 514/8

[56] References Cited

U.S. PATENT DOCUMENTS

| | | | |
|---|---|---|---|
| 4,017,471 | 4/1977 | Davies ............................ | 260/112 B |
| 4,046,722 | 9/1977 | Rowland ......................... | 424/85 X |
| 4,093,607 | 6/1978 | Sela et al. ....................... | 260/112 B |
| 4,263,279 | 4/1981 | Sela et al. ....................... | 424/85 |
| 4,315,851 | 2/1982 | Yoshikumi et al. ............. | 260/112 B |
| 4,340,535 | 7/1982 | Voisin et al. .................... | 260/112 B |
| 4,350,626 | 9/1982 | Masuho et al. ................. | 260/112 R X |
| 4,359,457 | 11/1982 | Neville, Jr. et al. ............. | 424/85 |
| 4,401,592 | 8/1983 | Yoshikumi et al. ............. | 260/112 B |
| 4,414,148 | 11/1983 | Jansen et al. ................... | 260/112 B |
| 4,487,714 | 12/1984 | Kato et al. ...................... | 260/112 B |
| 4,489,710 | 12/1984 | Spitler ............................. | 424/85 X |
| 4,493,793 | 1/1985 | Chu ................................. | 260/112 P |

OTHER PUBLICATIONS

Biochem. Soc. Trans., 10(6), 1982, p. 505, Melino et al.
Europ. J. Cancer, 13 (1977), 593–596, Rowland.
Int. J. Cancer, 21 (1978), 747–755, Hurwitz et al.
Cancer Research, 41, 2700–2706 (1981), Kulkarni et al.
J. Natl. Cancer Institute, 60 (1978), 379–384, Bernstein et al.
Chem. Pharm. Bull, vol. 29, 1981, pp. 844–848, JP; T. Suzuki: "The Preparation of Mitomycin C, Adriamycin and Daunomycin Covalently Bound to Antibodies as Improved Cancer Chemotherapeutic Agents".
Chem. Abstracts, vol. 99, 1983, p. 30, No. 169139g, P. Hazarika et al.: "Protein–Bound Daunorubicin as an Agent for Cancer Therapy".
Chemical Abstracts, vol. 95, 1981, p. 27, No. 73122n, P. N. Kulkarni et al.: "Covalent Binding of Methotrexate to Immunoglobulins and the Effect of Antibody-Linked Drug on Tumor Growth in Vivo".
Chemical Abstracts, vol. 92, 1980, p. 58, No. 104379w, J. Tai et al.: "Tumor Inhibition by Chlorambucil Covalently Linked to Antitumor Globulin".
Biological Abstracts, vol. 62, 1976, No. 44481, E. Hurwitz et al., "FAB Dimers of Antitumor Immunoglobulins as Covalent Carriers of Daunomycin".

*Primary Examiner*—Howard E. Schain
*Attorney, Agent, or Firm*—Oblon, Fisher, Spivak, McClelland & Maier

[57] ABSTRACT

Disclosed herein are an anti-tumor substance obtained by bonding an anti-tumor agent to human immunoglobulin, and a process for producing the same.

21 Claims, No Drawings ately administered as compared to the
ANTI-TUMOR SUBSTANCE OF IMMUNOGLOBULIN AND MELPHALAN AND PROCESS FOR PRODUCING THE SAME This application is a continuation of application Ser. No. 595,037, filed Mar. 29, 1984, now abandoned.

BACKGROUND OF THE INVENTION

The present invention relates to an anti-tumour substance obtained by bonding an anti-tumour agent to human immunoglobulin and a process for preparing the same.

Recently, with the development of immunochemistry, a large number of tumour-related antigen have been discovered and the tumour-specific antibody which selectively bonds to these tumour-related antigens has been developed. Further, trials are now under way wherein an anti-tumour agent is bonded to the tumour-specific antibody and the thus formed substance is administered to the patient suffering from the tumour for transferring the substance collectively to the portion of the tumour. In this trial, the tumour-specific antibody is prepared by a technique of immunizing a rabbit, horse and sheep with the tumour cells or the tumour-related antigen and is obtained from the serum of the thus immunized animal as an immunoglobulin fraction. In more recent years, after immunizing a mouse with the tumour cells or the tumour-related antigen, the antigen-producing cells are taken out from the mouse and the thus collected cells are subjected to cell fusion with the mouse-myleloma cells such as NS-1, thereby obtaining the monochronal cells producing anti-tumour antibody, and the anti-tumour antibody is taken out from the cells.

Although the trials are carried out with the anti-tumour antibody itself or the substance produced by bonding a certain cytotoxic substance to the anti-tumour antibody, the method has not been carried out practically, because the anti-tumour antibody is a heteroprotein to human, since the antibody has been obtained by immunizing a heterospecific animal. Namely, in the case where the antibody obtained from a heterospecific animal is administered to a person, the occurrence of a serum disease such as anaphylaxis, etc. on the second and successive administration cannot be evitable. In short, such an anti-tumour antibody can be used only once, and such a fact is the largest demerit of the method. It is necessary to use a homospecific antibody for overcoming the demerit, and the monochronal antibody prepared by using human lymphocytes is the ideal, however, such an antibody has not been provided.

Accordingly, it has been necessary for improving the demerits and solving the affairs concerning the practicality of such a method to investigate the homospecific antibodies and select those assembling to the tumour cells.

The present inventors, as a result of examination of the distribution of the various $^{125}I$-labelled antibodies in living body, have found that the general natural antibodies arrive at the portion of tumour and remain there for a long period of time and accordingly, the present inventors have known that in the case where after bonding an anti-tumour agent to the immunoglobulin, the thus obtained substance is administered to the cancer-bearing individual, the anti-tumour agent remains for a long period in the portion of the tumour, thereby exhibiting the anti-tumour effect. The present invention has been attained on these findings.

The anti-tumour substance obtained by bonding an anti-tumour agent to human immunoglobulin according to the present invention has the largest specificity and merit in that the anti-tumour substance obtained by bonding the anti-tumour agent to human immunoglobulin can be frequently administered as compared to the known product produced by bonding the anti-tumour agent to the anti-tumour antibody derived from the animal of different species from human, and remains at the portion of tumour for a long period of time.

Accordingly, the present invention provides a new type of medicines, which contains the anti-tumour substance produced by bonding an anti-tumour agent to human immunoglobulin and is highly practical.

SUMMARY OF THE INVENTION

In a first aspect of the present invention, there is provided an anti-tumour substance obtained by bonding an anti-tumour agent to human immunoglobulin.

In a second aspect of the present invention, there is provided a process for producing an anti-tumour substance comprising dissolving the anti-tumour agent in an aqueous solvent, after adding a bonding agent in the thus formed aqueous solution, adding human immunoglobulin in the thus prepared aqueous solution, thereby reacting the globulin with the anti-tumour agent at $-30°$ to $50°$ C. for one min to 48 hours, and purifying the thus formed reaction product by at least one means of purification selected from the group consisting of salting out, precipitation, recrystallization, elution and column-fractionation, to produce the anti-tumour substance obtained by bonding an anti-tumour agent to human immunoglobulin.

In a third aspect of the present invention, there is provided a pharmaceutical composition in dosage unit form comprising as an active ingredient an anti-tumour substance obtained by bonding an anti-tumour agent to human immunoglobulin.

In a fourth aspect of the present invention, there is provided a method for treating tumour, which comprises administering an effective amount of a substance obtained by bonding an anti-tumour agent to human immunoglobulin.

DETAILED DESCRIPTION OF THE INVENTION

The present invention relates to an anti-tumour substance obtained by bonding an anti-tumour agent to human immunoglobulin, and relates to a process for producing an anti-tumour substance comprising dissolving an anti-tumour agent in an aqueous solvent, after adding a bonding agent in the thus prepared solution, adding human immunoglobulin into the mixture, thereby reacting the human immunoglobulin with the anti-tumour agent at $-30°$ to $50°$ C. for a period of from one min to 48 hours, subjecting the thus formed reaction product to at least one of the purifying procedures selected from the group consisting of salting-out, precipitation, recrystallization, elution and column-fractionation, thereby obtaining the anti-tumour substance in which the anti-tumour agent has been bonded to human immunoglobulin, and further relates to a pharmaceutical composition in dosage unit form comprising as an active ingredient the anti-tumour substance in which the anti-tumour agent has been bonded to human immunoglobulin, and also relates to a method for treating tumour, comprising administering an effective amount of the anti-tumour substance in which the anti-tumour agent has been bonded to human immunoglobulin.

The anti-tumour substance according to the present invention is the product of bonding a highly cytotoxic, anti-tumour agent belonging to the group consisting of alkylating agents such as chlorambucil, melphalan, ACNU, cyclophosphamide and the like, antibiotics such as mitomycin C, doxorubicin hydrochloride, daunorubicin hydrochloride, bleomycin, actinomycin D, neocarcinostatin and the like, and antimetabolites such as cytarabine, 8-azaguanine, 5-fluorouracil, methotrexate, sodium aminopterin, 6-mercaptopurine and the like to human immunoglobulin under extremely mild reaction conditions, and is an anti-tumour substance which is excellent in anti-tumour effects in spite of its remarkably low cytotoxicity as compared to that of the anti-tumour agent which is one of the starting materials of the present substance.

Recently, various anti-tumour agents have been broadly used, thereby exhibiting a certain degree of effects. As the anti-tumour agent, chlorambucil, melphalan, ACNU, cyclophosphamide, cytarabine, 8-azaguanine, 5-fluorouracil, methotrexate, sodium aminopterin, mitomycin, daunorubicin, actinomycin D and sarkomycin are used, however, each of these substances has a high cytotoxicity, and it has been known that after being administered with the substance, a side effect such as leucocytepenia, depilation and gastroenteric disorder appears on the patient administered with the substance and accordingly, there is actually a limit of using the substance as a medicine.

On the other hand, trials have been carried out wherein an antibody to the tumour cell or the tumour-related antigen is prepared or isolated and the thus prepared or isolated cells or antigen is used in the treatment of the tumour, however, favorable effects have not been obtained. Furthermore, quite recently, it has been proposed that an anti-tumour effect is expected in a new substance obtained by chemically bonding an anti-tumour agent to an anti-tumour antibody. However, since the conditions of reaction for obtaining such a substance are too severe, any sufficient results have not been obtained. Further, in the above-mentioned experiment, antibody obtained from an animal different in species from human was used and accordingly, the side effect of the heterospecific antibody such as serum disease was inevitable.

Accordingly, the present inventors have found a method for purifying the anti-tumour antibody obtained from a heterospecific animal by affinity chromatography (refer to Japanese Patent Application Laying-Open Nos. 55-092325 (1980), 56-065828 (1981) and 56-065829 (1981)). By the thus found method, a highly purified antibody is obtained, however, there is still a problem in the case of carrying out frequent administration.

As a result of examining the attainability of several antibodies to the portion of a tumour, it has been found by the present inventors that a naturally obtainable antibody obtained by affinity chromatography can attain the portion of the tumour at a high concentration and can remain therein for a longer period of time in other organs, and based on their finding, each of the following anti-tumour agents was bonded to human immunoglobulin:

Chlorambucil, melphalan, ACNU, cyclophosphamide, cytarabin, 8-azaguanine, 5-fluorouracil, methotrexate, sodium aminopterin, mitomycin C, doxorubicin hydrochloride, bleomycin, daunorubicin, actinomycin D and sarkomycin.

The thus obtained substances were found to exhibit respectively a favorable anti-tumour effect, and because of the easiness of synthesis and high stability of melphalan and esters thereof, the most preferable bonded substance was those derived from melphalan and esters thereof. For reference, the naturally obtainable antibody contains human immunoglobulin (Ig) and an antibody (F(ab')$_2$) of a low molecular weight.

The bonding of human immunoglobulin and an anti-tumour substance is carried out by the following method.

The anti-tumour agent to be bonded to human immunoglobulin is dissolved in an aqueous solvent selected from an aqueous acidic solution, an aqueous alkaline solution, an aqueous neutral solution and an aqueous phosphoric buffer solution containing sodium borate and the like. A bonding agent selected from the group consisting of carbodiimide, dextran, glutaraldehyde, diethylmalonimidate, isocyanate and polyglutamic acid is added to the solution, and the reaction is carried out by adding human immunoglobulin (containing also F(ab')$_2$) into the mixture at $-30°$ to $+50°$ C., preferably 0° to 30° C. for one min to 48 hours, preferably 10 min to 25 hours.

The reaction product was purified by a means of salting-out, precipitation, recrystallization, elution, column fractionation, thereby obtaining the anti-tumour substance comprising the anti-tumour agent bonded to human immunoglobulin.

The acute toxicity of the thus obtained anti-tumour substance (hereinafter referred to as the present substance) was examined by injecting thereof intravenously to a group of mice at a dose rate of 4000 mg/kg, however, no death could be observed in a week after injection.

The acute toxicity was further examined on the anti-tumour substances obtained by bonding an anti-tumour agent to the antibody of low molecular weight which has been obtained by enzymatic hydrolysis of human immunoglobulin with pepsin (refer to Nisonoff, Science, 132, 1770(1970)), plasmin (Sgouris, Vox Sang, 18, 71(1967)), thermolysin (refer to Japanese Patent Application Laying Open No. 51-95125), papain, trypsin or chymotripsin. In the above-mentioned case of bonding the anti-tumour substance to the antibody of low molecular weight, for instance, F(ab')$_2$, the intravenous injection of 4000 mg/kg thereof did not kill the thus treated mice within a week.

Accordingly, the present substance is extremely low toxic and can be administered frequently, and it is effective in treatment of human cancers, for instance, acute leukemia, malignant lymphoma, carcinoma, sarcoma, malignant chorionepthelioma, acute myelogenous leukemia, melanoma, acute lymphatic leukemia and myeloma; head and neck cancer, upper gastrointestinal cancer, colorectal carinoma, pancreatic carinoma and malignant hepatomas, endocrine tumors, genitourinary tumors, gynecological tumors, breast cancer, leukemias and myeloma and malignant melanoma; and lung cancer, esophagus cancer, breast cancer, stomach cancer, colon cancer, rectal cancer, hepatic cancer (hepatoma), renal cancer, ovarian cancer, uterus cervical cancer and leukemias and myeloma.

As a method of formulating in the case where the present substance is used as an anti-tumour agent or an active ingredient of a pharmaceutical composition, and as a method of administering the composition, the respective known methods can be applied. As a route of administration, oral, injective or rectal may be mentioned. As the form of the composition comprising the present substance, powder, granule, tablet, injection and suppository may be mentioned, however, the administration is preferably carried out by the tablet or injection. For formulating the composition for injection, an aqueous solvent such as aqueous physiological saline solution, sterilized water, Ringer's solution, etc., non water-soluble solvents, isotonic agents, indolentic agent, stabilizers, antiseptics, suspension stabilizer, buffer, emulsifier may be optionally used therein.

An example for formulation of the composition according to the present invention is shown as follows.

After preparing 50 ml of an aqueous solution of 1 g of the present substance and 5 g of mannitol and sterilizing the solution in an ordinary method, the sterilized solution is divided into vials for injection, or freeze-dried as it is to be a composition for injection, which is diluted with an aqueous physiological saline solution on injection. Generally, the content of the present substance in the composition is 0.01 to 90 % by weight, preferably 0.1 to 60% by weight.

The amount of administration of the present substance depends on the conditions of the patient, however, it is generally 0.1 to 10 g/day/60 kg, preferably 1 to 6 g/day/60 kg.

According to the present invention, since the anti-tumour activity of the anti-tumour agent and the tumour-tropic property of the human immunoglobulin of the enzyme-treated human immunoglobulin are retained in the anti-tumour substance of the present invention without losing, the present substance, when administered, arrives at the intended site of tumour effectively, remains there for a long period of time to exhibit the anti-tumour effect.

Since it is not necessary to select the antibody from the anti-tumour antibody in the case of the synthesizing the present substance, the present invention is to be very advantageous industrially.

The present invention will be more precisely explained while referring to Examples as follows.

However, the present invention is not restricted to Examples under mentioned. From the foregoing description, one skilled in the art can easily ascertain the essential characteristics of the present invention, and without departing from the spirit and scope thereof, can make various changes and modifications of the present invention to adapt it to various usages and conditions.

EXAMPLE 1

Examination of the Distribution of Human Immunoglobulin

In order to examine what kind of the antibodies is practically usable according to the process of the present invention, the distribution of each of the $^{125}I$-labelled-anti-S-180 rabbit immunoglobulin, $^{125}I$-labelled-normal ICR mouse immunoglobulin and $^{125}I$-labelled-human immunoglobulin was administered to a S-180 cancer-bearing mouse, and the distribution of each of the administered $^{125}I$-labelled immunoglobulins was detected as follows.

Each of the immunoglobulins was labelled by $^{125}I$ in the protein moiety thereof by the method of W. H. Hurter et al. (refer of Biochem. J., 89, 114 (1963)). For instance, mitomycin C bonded to anti-S-180 antibody (rabbit immunoglobulin) was dissolved in aqueous 0.5M phosphoric acid buffer solution of pH of 7.4 so as to obtain a concentration of 5 mg/ml and after introducing 0.5 ml of the solution in a Spick tube, $Na^{125}I$ was added to the solution in an amount of 0.25 mCi. To the mixture, 0.7 mg of chloramin T dissolved in 200 μl of aqueous 0.05M phosphoric acid buffer solution was added to carry out a reaction at 0° C. for 15 min. Thereafter, by adding 10 mg of potassium iodide and 1.75 mg of sodium pyrosulfite dissolved in aqueous 0.05M phosphoric acid buffer solution to stop the reaction. By passing the reaction mixture through a column of Sephadex G-25 (2.2 cm in inner diameter and 40 cm in height), the un-reacted radioactive iodine and the reagents were removed to obtain $^{125}I$-labelled mitomycin bonded to anti-S-180 rabbit immunoglobulin. In the same manner, $^{125}I$-labelled mitomycin bonded to normal ICR mouse immunoglobulin and $^{125}I$-labelled mitomycin bonded to human immunoglobulin.

To a group of S-180 cancer-bearing ICR mice (after 2 weeks of transplantation of S-180 cancer), each of the thus prepared $^{125}I$-labelled mitomycin C bonded to the respective immunoglobulins was intravenously administered, and after sacrificing the animals after 24 and 144 hours of the administration, the blood, the portion of S-180 cancer, the liver, the kidney, the intestine were extirpated and the radioactivity of the thus extirpated part or organ was examined by γ-counter of well-type to calculate the amount of each of the thus prepared $^{125}I$-labelled mitomycin C bonded to the respective immunoglobulin per unit weight of the part or the organ.

From the thus obtained amounts, the distribution of the substance in living body of the thus treated animal after 24 hours of administration was known as are shown in Table 1.

TABLE 1

| Kind of antibody | Accumulation in tumour*1 | Ratio*2 | | |
|---|---|---|---|---|
| | | Tumour/Kidney | Tumour/Liver | Tumour/Intestine |
| 1*3 | 3.6 | 6.0 | 9.0 | 12.0 |
| 2 | 0.6 | 2.8 | 1.5 | 8.4 |
| 3 | 1.9 | 1.9 | 3.8 | 19.0 |

Notes:
*1: $\dfrac{\text{Antibody in tumour}}{\text{Total antibody administered} \times \text{Tumour weight}} \times 100$

*2: $\dfrac{\% \text{ accumulation in tumour}}{\% \text{ accumulation in other tissue}}$

*3: 1: Anti-S-180 rabbit immunoglobulin
2: Normal ICR-mouse immunoglobulin
3: Human immunoglobulin.

In the same manner, by counting the radioactivity of the organs extirpated after 144 hours of administration, the percentage by weight of the remaining substance in each organ to the total amount of remaining substance in the body of the animal was obtained as shown in Table 2.

TABLE 2

| | Organs or the site of the tumour | | | | | Unit: % by weight |
|---|---|---|---|---|---|---|
| Kind of antibody | Portion of tumour | Liver | Kidney | Spleen | Intestine | Others |
| 1*1 | 66.6 | 7.4 | 11.1 | 5.6 | 1.9 | 7.4 |
| 2 | 41.3 | 27.9 | 4.2 | 20.9 | 2.1 | 3.6 |

TABLE 2-continued

| Kind of antibody | Organs or the site of the tumour Unit: % by weight | | | | |
|---|---|---|---|---|---|
| | Portion of tumour | Liver | Kidney | Spleen | Intestine | Others |
| 3 | 38.7 | 10.2 | 20.4 | 10.2 | 2.0 | 18.5 |

Note: *1:
1: Anti-S-180 rabbit immunoglobulin
2: Normal ICR-mouse immunoglobulin
3: Human immunoglobulin.

The results show that the heterospecific antibody obtained by immunizing the heterospecific animal with a tumour antigen exhibits an excellent attainability to the tumour, however, it is also shown that the natural antibody of the same species remains in the portion of the tumour at a high rate as compared to the other organ, although the rate of attainability of the natural antibody is as low as 1/5 to 1/10 as compared to the attainability of the species-specific antibody. From these facts, it has been known by the present inventors that the natural antibody is high in practicality as a carrier.

EXAMPLE 2

Preparation of Human Immunoglobulin

In 1000 ml of serum of a normal healthy person, 1000 ml of aqueous 0.005M phosphoric acid buffer solution of sodium chloride (hereinafter referred to as PBS) were added to prepare a diluted serum, and to the diluted serum, 2000 ml of aqueous saturated solution of ammonium sulfate was added slowly under agitation. After leaving the mixture to stand still for 60 min at 4° C., a precipitate was salted out, and by subjecting the mixture to centrifugal separation at 8,000 rpm for 30 min, the precipitate was collected and dissolved in PBS to make the whole volume to 1,000 ml. By adding 250 ml of aqueous saturated solution of ammonium sulfate to the mixture, the degree of saturation of ammonium sulfate of the whole mixture was made to 20%. In the case where the mixture became turbid to form a precipitate, the whole mixture was subjected to centrifugation to remove the precipitate which was fibrinogen. Into the thus obtained supernatant liquid, 250 ml of aqueous saturated solution of ammonium sulfate were added to make the degree of saturation by ammonium sulfate of the whole mixture to 33%. After leaving the whole mixture to stand still for 60 min, the whole mixture was subjected to centrifugation at 8,000 rpm for 30 min to collect the precipitate. After dissolving the thus collected precipitate in 1,000 ml of PBS, 500 ml of aqueous saturated solution of ammonium sulfate were added to the solution. After stirring the whole mixture for 60 min, the whole mixture was subjected to centrifugation at 8,000 rpm for 30 min to collect the precipitate, and the thus collected precipitate was dissolbed in 300 ml of PBS. The solution was dialyzed against PBS to remove ammonium sulfate, and the dialyzate was subjected to column chromatography while using DEAE-cellulose column of 5 cm in diameter and 50 cm in height, thereby obtaining a fraction passed through at 0.005M and pH of 8.0. The fraction passed through the column was dialyzed against distilled water to remove the salt contained therein, and the dialyzate was subjected to freeze-drying to obtain 12.5 g of human immunoglobulin.

EXAMPLE 3

Preparation of the Substance Obtained by Bonding Immunoglobulin Derived from Normal Human to an Anti-Tumour Agent Each of mitomycin C, doxorubicin hydrochloride, daunorubicil hydrochloride, breomycin, actinomycin and sarkomycin was reacted with immunoglobulin derived from normal human to synthesize each of the present substances as shown in the following.

Bonding of Mitomycin C to Human Immunoglobulin

In 100 ml of distilled water, 1.0 g of human immunoglobulin was dissolved, and in the thus formed solution, 111.3 mg of mitomycin C was dissolved. After adjusting the pH of the solution to 5.5 with aqueous 1.0N hydrochloric acid, 262.6 mg of 1-ethyl-3-(3-dimethylaminopropyl)-carbodiimide hydrochloride was added thereto at 4° C. and after the following reaction time, the reaction was stopped by the addition of 5 ml of an acetic acid-sodium acetate buffer solution of pH of 5.5. After condensing and desalting the reaction mixture while using an ultrafilter to 10 ml, 10 ml of the thus obtained condensate was passed through a column of Sephadex G-25 (made by Pharmacia Japan Co.) of 5 cm in diameter and 90 cm in height to completely separate the high molecular weight substance and the low molecular weight substance. The supernatant solution obtained by subjecting the eluate to ultracentrifugation for 60 min at 40,000 G was freeze-dried at 0° C. to obtain the present substance as a product. The amount of bonded mitomycin C was determined by ultraviolet absorption at 360 nm and shown in Table 3.

TABLE 3

| Reaction time (hour) | Mitomycin C/human immunoglobulin (μg/mg) |
|---|---|
| 1 | 2.8 |
| 4 | 5.3 |
| 24 | 8.6 |

In the same manner as above, 1.0 g of human immunoglobulin was brought into reaction with each of doxorubicin hydrochloride, daunorubicin hydrochloride, bleomycin and actinomycin D to obtain about 800 mg of the respective substances.

The amount of bonded doxorubicin per mg of human immunoglobulin was 4.8 μg (in the case of reacting for 60 min) and 9.5 μg (in the case of reacting for 24 hours).

EXAMPLE 4

Each of the present substances was prepared by reacting immunoglobulin derived from a normal human with each of chlorambucil, melphalan (phenylaranine mustard), ACNU, uramustin, cyclophosphamide and melphalan methyl ester, according to amide-bonding as is shown in the following.

(4-1) Bonding Melpharan to Human Immunoglobulin

In 100 ml of distilled water, 1.0 g of human immunoglobulin was dissolved, and 100 mg of melphalan were suspended in the thus formed solution. After adjusting the pH of the aqueous suspension to 5.5 with the addition of aqueous 1.0N hydrochloric acid, 1-ethyl-3-(3-dimethylaminopropyl)-carbodiimide hydrochloride was added to the aqueous suspension to react for 24 hours. After stopping the reaction with the addition of 5 ml of aqueous acetic acid-sodium acetate buffer solution, the reaction mixture was condensed and desalted while using an ultrafilter to a volume of 10 ml and the condensate (10 ml) was passed through a column of Sephadex G-25 (made by Pharmacia Japan Co.) of 5 cm in diameter and 90 cm in height, thereby completely separate the high-molecular weight substances and the low-molecular weight substances.

After subjecting the eluate to ultracentrifuge of 40,000 G for 60 min, the supernatant liquid was freeze-dried at 0° C. to obtain the present substance. The content of protein in the thus obtained present substance was determined by the Copper-Folin Method while using albumin as the standard, and the alkylation activity of the present substance was determined by the method of Epstein (refer to Epstein, J. Anal. Chem., 27, 1423 (1955)), and as the result, it was found that 6 $\mu$g of melpharan bonded to 1 mg of human immunoglobulin.

(4-2) Bonding Chlorambucil, ACNU or Uramustine to Human Immunoglobulin

In the similar procedures to that in 4-1, 1.0 g of human immunoglobulin was brought into reaction to each of chlorambucil, ACNU and uramustine to obtain about 900 mg of each of the present substances. The amount of chlorambucil bonded to 1 mg of human immunoglobulin was 5.1 $\mu$g after reacting for 60 min and 11.7 $\mu$g after reacting for 24 hours.

(4-3) Bonding Methyl Ester of Melphalan to Human Immunoglobulin

After dissolving 1.0 g of human immunoglobulin in 100 ml of distilled water, 100 mg of hydrochloride of methyl ester of melphalan were dissolved in the thus prepared solution, and while adjusting the pH of the solution to 5.5 with the addition of aqueous 1.0N hydrochloric acid solution, 1-ethyl-3-(3-dimethylaminopropyl)-carbodiimide hydrochloride was added to react for 24 hours. After stopping the reaction with the addition of 5 ml of aqueous acetic acid-sodium acetate buffer solution of pH of 5.5 to the reaction mixture, the reaction mixture was condensed and desalted to 10 ml by the use of an ultrafilter. Ten milliliters of the thus condensed and desalted liquid was passed through a column of Sephadex G-25 (made by Pharmacia Co.) of 5 cm in diameter and 90 cm in height, thereby separating the high-molecular weight substances and the low-molecular weight substances in the reaction liquid completely. The eluate was subjected to ultracentrifugation at 40,000 G for 60 min, and the supernatant liquid was freeze-dried at 0° C. to obtain the present substance. The amount of methyl ester of melpharan bonded to 1 mg of human immunoglobulin was 10 $\mu$g.

EXAMPLE 5

Immunoglobulin derived from normal human was reacted with each of cytarabine, 8-azaguanine, 5-fluorouracil, methotrexate and aminopterin sodium to obtain each of the compounds forming an amide bonding as shown in the following example.

(5-1) Bonding of Methotrexate to Human Immunoglobulin

After dissolving 1.0 g of human immunoglobulin in 100 ml of distilled water, 151.3 mg of methotrexate were dissolved in the thus prepared solution, and while adjusting the pH of the solution to 5.5 with the addition of aqueous 1.0N hydrochloric acid solution, 1-ethyl-3-(3-dimethylaminopropyl)-carbodiimide hydrochloride was added to react for 24 hours. After stopping the reaction with the addition of 5 ml of aqueous acetic acid-sodium acetate buffer solution of pH of 5.5 to the reaction mixture, the reaction mixture was condensed and desalted to 10 ml by the use of an ultrafilter. Ten milliliters of the thus condensed and desalted liquid was passed through a column of Sephadex G-25 (made by Pharmacia Co.) of 5 cm in diameter and 90 cm in height, thereby separating the high-molecular weight substances and the low-molecular weight substances in the reaction liquid completely. The eluate was subjected to ultracentrifugation at 40,000 G for 60 min, and the supernatant liquid was freeze-dried at 0° C. to obtain the present substance. The amount of methotrexate bonded to 1 mg of human immunoglobulin determined by utilizing the ultraviolet absorption at 305 nm was 10 $\mu$g.

(5-2) Bonding of Cytarabine, 8-Azaguanine, 5-Fluorouracil or Aminopterin Sodium to Human Immunoglobulin After dissolving 1.0 g of human immunoglobulin in 100 ml of distilled water, 100 mg of each of cytarabine, 8-azaguanine, 5-fluorouracil and aminopterin sodium were dissolved in the thus prepared solution, and while adjusting the pH of the solution to 5.5 with the addition of aqueous 1.0N hydrochloric acid solution, 1-ethyl-3-(3-dimethylaminopropyl)-carbodiimide hydrochloride was added to react for 24 hours. After stopping the reaction with the addition of 5 ml of aqueous acetic acid-sodium acetate buffer solution of pH of 5.5 to the reaction mixture, the reaction mixture was condensed and desalted to 10 ml by the use of an ultrafilter. Ten milliliters of the thus condensed and desalted liquid was passed through a column of Sephadex G-25 (made by Pharmacia Co.) of 5 cm in diameter and 90 cm in height, thereby separating the high-molecular weight substances and the low-molecular weight substances in the reaction liquid completely. The eluate was subjected to ultracentrifugation at 40,000 G for 60 min, and the supernatant liquid was freeze-dried at 0° C. to obtain about 900 ml of each of the present substances. The amount of cytarabine bonded to 1 mg of human immunoglobulin was 4.7 $\mu$g after reaction of 60 min and 8.3 $\mu$g after reaction of 24 hours.

EXAMPLE 6

Bonding of an Anti-tumour Agent to Human Immunoglobulin F(ab')$_2$ (6-1) Preparation of Human Immunoglobulin F(ab')$_2$ After dissolving 1 g of human immunoglobulin into 100 ml of aqueous 0.1N sodium acetate buffer solution of pH of 4.5, pepsin was added to the thus prepared solution so as to make the weight ratio of the enzyme to the protein to be 1:100 in the solution, and the digestion was carried out at 37° C. for 16 hours. After stopping the reaction by adding solid tris-hydrochloride so as to make the pH of the reaction mixture to 8.0, the reaction liquid was condensed to 10 ml by the use of an ultrafilter. Five milliliters of the condensate were charged into a column of Sephadex G-150 (made by Pharmacia Co.) of 5 cm in diameter and 90 cm in height and eluted the adsorbed matter by PBS of pH of 7 of the thus obtained three peaks, the first peak was collected as F(ab')$_2$. After filling the thus collected fraction into a dialysis tube, the fraction was subjected to desalting and then freeze-drying to obtain human immunoglobulin F(ab')$_2$.

(6-2) Bonding an Anti-tumour Agent to Human Immunoglobulin F(ab')$_2$

After dissolving 500 mg of the thus obtained human immunoglobulin F(ab')$_2$ in 50 ml of distilled water, 55.6 mg of mitomycin C were dissolved in the thus prepared solution. While adjusting the pH of the solution to 5.5 with the addition of aqueous 1.0N hydrochloric acid solution, 131.3 mg of 1-ethyl-3-(3-dimethylaminopropyl)-carbodiimide hydrochloride was added to the solution at 4° C. to make the reagents react together for the under-mentioned time period, and then the reaction was stopped by the addition of 5 ml of aqueous acetic acid-sodium acetate buffer solution. After condensing the reaction liquid to 5 ml by the use of an ultrafilter, the condensate was passed through a column of Sephadex G-25 (made by Pharmacia Co.) of 5 cm in diameter and 90 cm in height to completely separate the high-molecular weight substances and the low-molecular weight substances in the condensate. After subjecting the eluate to ultracentrifugation at 40,000 G for 60 min, the supernatant liquid was freeze-dried at 0° C. to obtain the present substance. The amount of mitomycin C bonded to human immunoglobulin F(ab')$_2$ determined by utilizing the ultraviolet absorption at 360 nm was shown in Table 4-1 as a function of the reaction time.

TABLE 4-1

| Reaction time (hour) | Mitomycin C/Human immunoglobulin F(ab')$_2$ ($\mu$g/mg) |
|---|---|
| 1 | 3.4 |
| 4 | 6.7 |
| 24 | 10.3 |

(6-3) Bonding Another Anit-tumour Agent to Human Immunoglobulin F(ab')$_2$

In a quite similar manner to that in 6-2, each of the anti-tumour agents shown in Table 4-2 was reacted with human immunoglobulin F(ab')$_2$ to obtain each of the present substance.

TABLE 4-2

| Anti-tumour agent | Yield of the present substance |
|---|---|
| Doxorubicin hydrochloride | about 800 mg |
| Daunorubicin hydrochloride | about 800 mg |
| Bleomycin | about 800 mg |
| Actinomycin D | about 800 mg |
| Chlorambucil | about 400 mg |
| Melphalan | about 400 mg |
| ACNU | about 400 mg |
| Uramustine | about 400 mg |
| Methyl ester of Melphalan | about 400 mg |
| Cyclophosphamide | about 400 mg |
| Cytarabine | about 400 mg |
| 8-Azaguanine | about 400 mg |
| 5-Fluorouracil | about 400 mg |
| Methotrexate | about 400 mg |
| Aminopterin sodium | about 400 mg |

In addition, the respective amounts of doxorubicin hydrochloride, melphalan and methotrexate to one milligram of humna immunoglobulin F(ab')$_2$ as the respective functions of reaction time were shown in Table 4-3.

TABLE 4-3

| | Unit: $\mu$g Reaction time (hour) | |
|---|---|---|
| Anti-tumour agent | 1 | 24 |
| Doxorubicin hydrochloride | 8.5 | 19.6 |

TABLE 4-3-continued

| | Unit: $\mu$g Reaction time (hour) | |
|---|---|---|
| Anti-tumour agent | 1 | 24 |
| Melphalan | 8.1 | 17.6 |
| Methotrexate | 7.5 | 17.3 |

EXAMPLE 7

Production of the Present Substance by the Use of Dextran and Glutaraldehyde as the Bonding Agent In 500 ml of distilled water, 500 mg of dextran was dissolved, and after adjusting the pH of the solution to 11 by the addition of aqueous 1N sodium hydroxide solution, a solution of 250 mg of bromcyan in 1 ml of acetonitrile was rapidly added to the alkaline solution under agitation and the pH of the mixture was adjusted to 10.8 to 11.0 by the addition of aqueous 1N sodium hydroxide solution and the pH was maintained for 10 min after addition of bromcyan. Thereafter, 100 mg of hexamethylenediamine dissolved in 2.5 ml of water were added to the mixture and the pH of the whole mixture was adjusted to 9.0 by the addition of aqueous 1N hydrochloric acid solution.

After stirring the mixture for 5 min, 250 mg of melphalan were added to the mixture, and the pH of the reaction mixture was reduced to 6.5 by the addition of aqueous 1N hydrochloric acid and the reduced pH was maintained for 15 min. Then, the reaction mixture was condensed at 4° C. to 10 ml. The whole amount of the condensate was passed through a column of Sephadex G-25 (made by Pharmacia Japan Co.) of 5 cm in diameter and 90 cm in height to separate the substance of high molecular weight and the substance of low molecular weight completely, and the eluate was subjected to ultracentrifugation at 40,000 G for 60 min and the thus obtained supernatant liquid was freeze-dried at 0° C. to obtain a compound formed by bonding 30 to 50 molecules of melphalan to one molecule of dextran.

By using 100 mg of the thus obtained compound and 100 mg of human immunoglobulin F(ab')$_2$ while bonding the two by glutaraldehyde, one of the present substance according to the present invention was obtained.

In a quite similar manner to that shown above except for using 250 mg of mitomycin C instead of 250 mg of melphalan, a compound formed by bonding 30 to 50 molecules of mitomycin C to one molecule of dextran was obtained, and using 100 mg of the thus obtained compound and 100 mg of human immunoglobulin F(ab')$_2$, another of the present substance was obtained in the presence of 100 g/ml of glutar aldehyde in the system at room temperature.

In a quite similar manner to that shown above except for using 250 mg of methotrexate instead of 250 mg of mitomycin C, a compound formed by adding 30 to 50 molecules of methotrexate to one molecule of dextran was obtained. By bonding 100 mg of the thus obtained compound to 120 mg of human immunoglobulin F(ab')$_2$ in the presence of 100 $\mu$g/ml of glutaraldehyde (at the final concentration), still another one of the present substances according to the present invention was obtained. In addition, by using human immunoglobulin instead of human immunoglobulin F(ab')$_2$, a different one of the present substances was obtained.

EXAMPLE 8

Production of the Present Substance by Only Using Glutar Aldehyde as the Bonding Agent In 1 ml of aqueous 0.01M phosphoric acid buffer solution of pH of 6.8, 11.3 mg of mitomycin C were dissolved, and 20 µl of an aqueous 1% by weight solution of glutaraldehyde was added to the thus prepared solution, and the mixture was stirred for 8 hours at room temperature. Then, a solution of 100 mg of human immunoglobulin dissolved in 20 ml of aqueous phosphoric acid buffer solution of pH of 6.8 was added to the mixture to carry out the reaction for 2 hours at room temperature. The reaction mixture was passed through a column of Sephadex G-25 (made by Pharmacia Japan Co.) of 5 cm in diameter and 90 cm in height to separate the substance of high molecular weight and the substance of low molecular weight completely. After subjecting the eluate to ultracentrifugation at 40,000 G for 60 min, the supernatant liquid was freeze-dried at 0° C. to obtain one of the present substances in which 9.6 µg of mitomycin C was bonded to 1 mg of human immunoglobulin.

In a quite similar manner to that shown above except for using 196 mg of adriamycin instead of 11.3 mg of mitomycin C, another one of the present substances was obtained in which 5.6 µg of adriamycin was bonded to one mg of human immunoglobulin.

In a quite similar manner to that shown above except for using 200 mg of methotrexate instead of 11.3 mg of mitomycin C, and using 100 mg of human immunoglobulin F(ab')$_2$ instead of 100 mg of human immunoglobulin, still another one of the present substances was obtained in which 7.8 µg of methotrexate was bonded to one mg of human immunoglobulin F(ab')$_2$.

EXAMPLE 9

Production of the Present Substance by Diethylmalonimidate as a Bonding Agent

In 10 ml of aqueous 0.2M solution of sodium borate of pH of 9.3, 11.3 mg of mitomycin C and 100 mg of human immunoglobulin were dissolved. Thereto 5 mg of diethylmalonimidate was added, and the mixture was stirred for one hour at room temperature while keeping the pH of the mixture at 8.6. Then, 2.5 mg of diethylmalonimidate was further added to the reaction mixture and the stirring was carried out for one hour. After the reaction was over, the reaction mixture was brought to neutral and by adding aqueous saturated solution of ammonium sulfate to the reaction mixture, a compound obtained by bonding human immunoglobulin to mitomycin C was precipitated. After collecting the precipitate by subjecting the reaction mixture to centrifugation at 7,000 rpm, the precipitate was dissolved in 5 ml of aqueous 5 mM phosphoric acid buffer solution, and the thus obtained solution was dialyzed against distilled water until no ammonium sulfate became detected in the dialyzate (for 72 hours). The dialyzate was passed through a column of Sephadex G-25 ) of 5 cm in diameter and 90 cm in height to remove the substance of low molecular weight in the dialyzate completely. The eluate was freeze-dried at −20° C. to obtain one of the present substances of the present invention, in which 6.3 g of mitomycin C bonded to one mg of human immunoglobulin.

In a quite similar manner to that shown above, another one of the present substances according to the present invention wherein mitomycin was bonded to human immunoglobulin F(ab')$_2$ was obtained.

In a quite similar manner to that shown above, each of the present substances was obtained from 100 mg of human immunoglobulin and one of melphalan and aminopterin sodium in a yield of 85 mg.

EXAMPLE 10

Examination of Anti-Tumour Activity of the Present Substance

Examination of the anti-tumour activities of the present substances obtained by bonding an anti-tumour agent to human immunoglobulin or obtained by bonding the anti-tumour agent to human immunoglobulin F(ab')$_2$ was carried out by using three kinds of tumours while comparing to the anti-tumour activity of the anti-tumour agent as follows.

(10-1) Anti-tumour Activity to Sarcoma 180 Solid Tumour

Cells of mouse sarcoma-180 which had been subjected to repeated subculture on ICR mouse were transplanted subcutaneously in axillary part of each of 10 ICR mice of a group at a rate of $1 \times 10^6$ cells/animal, and to each of the thus treated mice, an aqueous solution of each of the known anti-tumour agents, an aqueous solution of each of the present substances respectively produced by bonding one of the known anti-tumour agents to human immunoglobulin or an aqueous solution of each of the present substances respectively produced by bonding one of the known anti-tumour agents to human immunoglobulin F(ab')$_2$ was intraperitoneously administered every other day for 10 times in total. After 5 days of the final administration, the mouse was sacrificed to extirpate the tumour(s) to be weighed. The average weight of the tumours($\overline{T}$) of the thus treated mice and the average weight of the tumours($\overline{C}$) of the control mice administered with an aqueous physiological saline solution instead of the agent or the present substance were treated in the following formula, thereby obtaining the anti-tumour activity of the administered substance, i.e., the activity of suppressing the proliferation of the transplanted tumour:

$$\text{Anti-tumour activity (\%)} = \left(1 - \frac{\overline{T}}{\overline{C}}\right) \times 100$$

The thus obtained anti-tumour activity of the present substance produced in Examples 3 to 6 is shown in Table 5 while comparing that of the anti-tumour agent used for producing the present substance.

TABLE 5

Anti-tumour Activity (Activity of suppressing the proliferation of Sarcoma-180 Solid Tumour)

| Substance administered | Amount of administration (mg/kg b.w.) Total | Calculated as the anti-tumour agent | Anti-tumour activity (%) |
|---|---|---|---|
| Mitomycin | 1 | 1 | 40 |
| Mitomycin + human immunoglobulin | 200 | 1 | 35 |
| Mitomycin + human immunoglobulin F(ab')$_2$ | 200 | 1 | 38 |
| Bleomycin | 0.5 | 0.5 | 45 |
| Bleomycin + human immunoglobulin | 100 | 0.5 | 40 |
| Bleomycin + human immunoglobulin F(ab')$_2$ | 100 | 0.5 | 42 |
| Doxorubicin | 2 | 2 | 50 |
| Doxorubicin + human immunoglobulin | 400 | 2 | 47 |
| Doxorubicin + human immunoglobulin F(ab')$_2$ | 400 | 2 | 49 |

(10-2) Anti-tumour Activity to Yoshida Sarcoma

Ascites cells of Yoshida sarcoma which had been subjected to subculture repeatedly while using Donryu rats were transplanted into the abdominal cavity of each of 10 Donryu rats of a group at the rate of $1 \times 10^6$ cells/animal, and from after 24 hours of the transplantation, an aqueous solution of an anti-tumour agent, an aqueous solution of a substance obtained by bonding the anti-tumour agent to human immunoglobulin or an aqueous solution of a substance obtained by bonding the anti-tumour agent to human immunoglobulin F(ab')$_2$ was administered every other day for 5 times in total intraperitoneally to the thus transplanted rat. Rats were observed to record the average survival days($\bar{T}$)(for rats administered with each agent), and the average survival days($\bar{C}$)(for rats administered only with an aqueous physiological saline solution instead of the agent). The rate of life-elongation was calculated by the formula:

$$\text{Rate of life-elongation (\%)} = \left( \frac{\bar{T}}{\bar{C}} \times 100 \right)$$

The results are shown in Table 6.

(10-3) Anti-tumour Activity to Mouse Leukemia P-388

Ascites cells of mouse leukemia P-388 which had been subjected to repeated subculture while using DBA/2 mouse were intraperitoneally transplanted to each of 10 DBA/2 mice of a group, and from after 24 hours of the transplantation, an aqueous solution of each of the anti-tumour agent, an aqueous solution of each of the substance obtained by bonding each of the anti-tumour agent to human immunoglobulin or an aqueous solution of each of the substance obtained by bonding each of the anti-tumour substance to human immunoglobulin F(ab')$_2$ was intraperitoneally administered once a day for continuous 5 days. The thus treated mice were observed to record the average survival days($\bar{T}$) of the mice administered with the agent or the substance, and the average survival days($\bar{C}$) of the control mice (administered with an aqueous physiological saline solution instead of the agent or the substance). The anti-tumour activity of the agent or the substance (Rate of Life-elongation) was calculated by the following formula.

$$\text{Rate of life-elongation (\%)} = \left( \frac{\bar{T}}{\bar{C}} \times 100 \right)$$

The results are shown in Table 7.

TABLE 6

Anti-tumour Activity (Rate of Life-Elongation)

| Substance administered | Amount of administration (mg/kg b.w.) Total | Calculated as the anti-tumour agent | Rate of Life-Elongation (%) |
|---|---|---|---|
| Chlorambucil | 1.0 | 1.0 | 259 |
| Chlorambucil + human immunoglobulin | 200 | 1 | 230 |
| Chlorambucil + human immunoglobulin* | 200 | 1 | 235 |
| Melphalan | 1.5 | 1.5 | 230 |
| Melphalan + human immunoglobulin | 300 | 1.5 | 200 |
| Melphalan + human immunoglobulin* | 300 | 1.5 | 190 |
| Melphalan methyl ester + human immunoglobulin | 300 | 1.5 | 220 |
| Melphalan methyl ester + human immunoglobulin* | 300 | 1.5 | 230 |
| Uramustine | 5 | 5 | 290 |
| Uramustine + human immunoglobulin | 1000 | 5 | 240 |
| Uramustine + human immunoglobulin* | 1000 | 5 | 260 |

Note:
*means human immunoglobulin F(ab')$_2$

TABLE 7

Anti-tumour Activity (Rate of Life-Elongation)

| Substance administered | Amount of administration (mg/kg b.w.) Total | Amount of administration (mg/kg b.w.) Calculated as the anti-tumour agent | Rate of Life-Elongation (%) |
| --- | --- | --- | --- |
| Cytarabine | 20 | 20 | 220 |
| Cytarabine + human immunoglobulin | 4000 | 20 | 190 |
| Cytarabine + human immunoglobulin* | 4000 | 20 | 195 |
| Methotrexate | 3 | 3 | 250 |
| Methotrexate + human immunoglobulin | 600 | 3 | 220 |
| Methotrexate + human immunoglobulin* | 600 | 3 | 235 |
| Aminopterin sodium | 3 | 3 | 270 |
| Aminopterin sodium + human immunoglobulin | 600 | 3 | 240 |
| Aminopterin sodium + human immunoglobulin* | 600 | 3 | 250 |
| Melphalan | 1.5 | 1.5 | 230 |
| Melphalan + Dextran + Human immunoglobulin | 15 | 1.5 | 210 |
| Melphalan + Dextran + Human immunoglobulin* | 15 | 1.5 | 220 |
| Adriamycin | 2 | 2 | 50 |
| Adriamycin + Human immunoglobulin | 20 | 2 | 48 |
| Adriamycin + Human immunoglobulin* | 20 | 2 | 46 |
| Mitomycin C | 1 | 1 | 40 |
| Mitomycin C + Human immunoglobulin | 10 | 1 | 35 |
| Mitomycin C + Human immunoglobulin* | 10 | 1 | 38 |

Note:
*Human immunoglobulin F(ab')$_2$

What is claimed is:

1. An anti-tumor substance manufactured by a process comprising:
   (a) dissolving melphalan or ester thereof in aqueous solvent;
   (b) adding a bonding agent, selected from the group consisting of carbodiimides, glutaraldehyde, diethylmalonimidate, isocyanate and polyglutamic acid, to the aqueous solution, and then adding human immunoglobulin obtained from a normal healthy person to said aqueous solution, and thereby reacting said human immunoglobulin and said melphalan or ester thereof at a temperature of −30° to 50° C. for 1 minute to 48 hours; and
   (c) subjecting the thus produced reaction product to purification by means of a method selected from the group consisting of salting out, precipitation, recrystallization, elution and column-fractionation.

2. The anti-tumor substance according to claim 1, wherein said bonding agent is a carbodiimide.

3. The anti-tumor substance according to claim 2, wherein said carbodiimide is one selected from the group consisting of 1-ethyl-3,3-dimethylaminopropyl carbodiimide, dicyclohexyl carbodiimide and morpholinoethyl carbodiimide.

4. The anti-tumor substance according to claim 1, wherein said ester is a lower alkyl ester.

5. The anti-tumor substance according to claim 4, wherein said lower alkyl ester is a methyl ester.

6. The anti-tumor substance according to claim 1, wherein said human immunoglobulin is IgG.

7. The anti-tumor substance according to claim 1, wherein said human immunoglobulin is F(ab')$_2$.

8. A pharmaceutical composition in dosage unit form comprising an effective amount of an anti-tumor substance obtained by bonding melphalan or ester thereof to human immunoglobulin derived from a normal healthy person using a bonding agent, selected from the group consisting of carbodiimides, glutaraldehyde, diethylmalonimidate, isocyanate and polyglutamic acid, as the active ingredient thereof.

9. The pharmaceutical composition according to claim 8, wherein said bonding agent is carbodiimide.

10. The pharmaceutical composition according to claim 9, wherein said carbodiimide is one selected from the group consisting of 1-ethyl-3,3-dimethylaminopropyl carbodiimide, dicyclohexyl carbodiimide and morpholinoethyl carbodiimide.

11. The pharmaceutical composition according to claim 8, wherein said ester is a lower alkyl ester.

12. The pharmaceutical composition according to claim 11, wherein said lower alkyl ester is a methyl ester.

13. The pharmaceutical composition according to claim 8, wherein said human immunoglobulin is IgG.

14. The pharmaceutical composition according to claim 8, wherein said human immunoglobulin is F(ab')$_2$.

15. A method for treating a tumor selected from the group consisting of human cancers of breast, lung, esophagus, stomach, colon, kidney, prostate, gallbladder and bone marrow, which comprises administering an effective amount of a compound obtained by bonding melphalan or ester thereof to human immunoglobulin derived from a normal healthy person using a bonding agent selected from the group consisting of carbodiimides, glutaraldehyde, diethylmalonimidate, isocyanate and polyglutamic acid.

16. The method according to claim 15, wherein said bonding agent is a carbodiimide.

17. The method according to claim 16, wherein said carbodiimide is one selected from the group consisting of 1-ethyl-3,3-dimethylaminopropyl carbodiimide, dicyclohexyl carbodiimide and morpholinoethyl carbodiimide.

18. The method according to claim 15, wherein said ester is a lower alkyl ester.

19. The method according to claim 18, wherein said lower alkyl ester is a methyl ester.

20. The method according to claim 15, wherein said human immunoglobulin is Ig G.

21. The method according to claim 15, wherein said human immunoglobulin is F(ab')$_2$.

UNITED STATES PATENT AND TRADEMARK OFFICE
CERTIFICATE OF CORRECTION

PATENT NO. : 4,738,843

DATED : April 19, 1988

INVENTOR(S) : YOSHIHARU OGUCHI ET AL

It is certified that error appears in the above-identified patent and that said Letters Patent is hereby corrected as shown below:

Column 1, line 22, change "transferring" to -- carrying --.

Column 8, line 55, change "uramustin" to --uramustine--.

Column 8, line 59, change "Melpharan" to --Melphalan--.

Column 9, line 21, change "4-1" to --(4-1)--.

Column 11, line 35, change "Anit-" to --Anti- --.

Column 14, line 30, change "to" to --against--.

Column 14, lines 45 to 46; column 15, lines 32 to 33 and column 16, lines 24 and 32, change "intraperitoneously" to --intraperitoneally--.

UNITED STATES PATENT AND TRADEMARK OFFICE
CERTIFICATE OF CORRECTION

PATENT NO. : 4,738,843
DATED : April 19, 1988
INVENTOR(S) : YOSHIHARU OGUCHI ET AL It is certified that error appears in the above-identified patent and that said Letters Patent is hereby corrected as shown below:

Column 14, line 57 and column 15, Table 5, line 2, change "proliferation" to --growth--.

Column 17, lines 50-51, column 18, lines 31-32 and 57, change "1-ethyl-3,3-dimethylaminopropyl carbodiimide" to --1-ethyl-3-(3-dimethylaminopropyl)-carbodiimide--.

Signed and Sealed this

Fourteenth Day of February, 1989

Attest:

DONALD J. QUIGG

Attesting Officer

Commissioner of Patents and Trademarks